Figure 1:
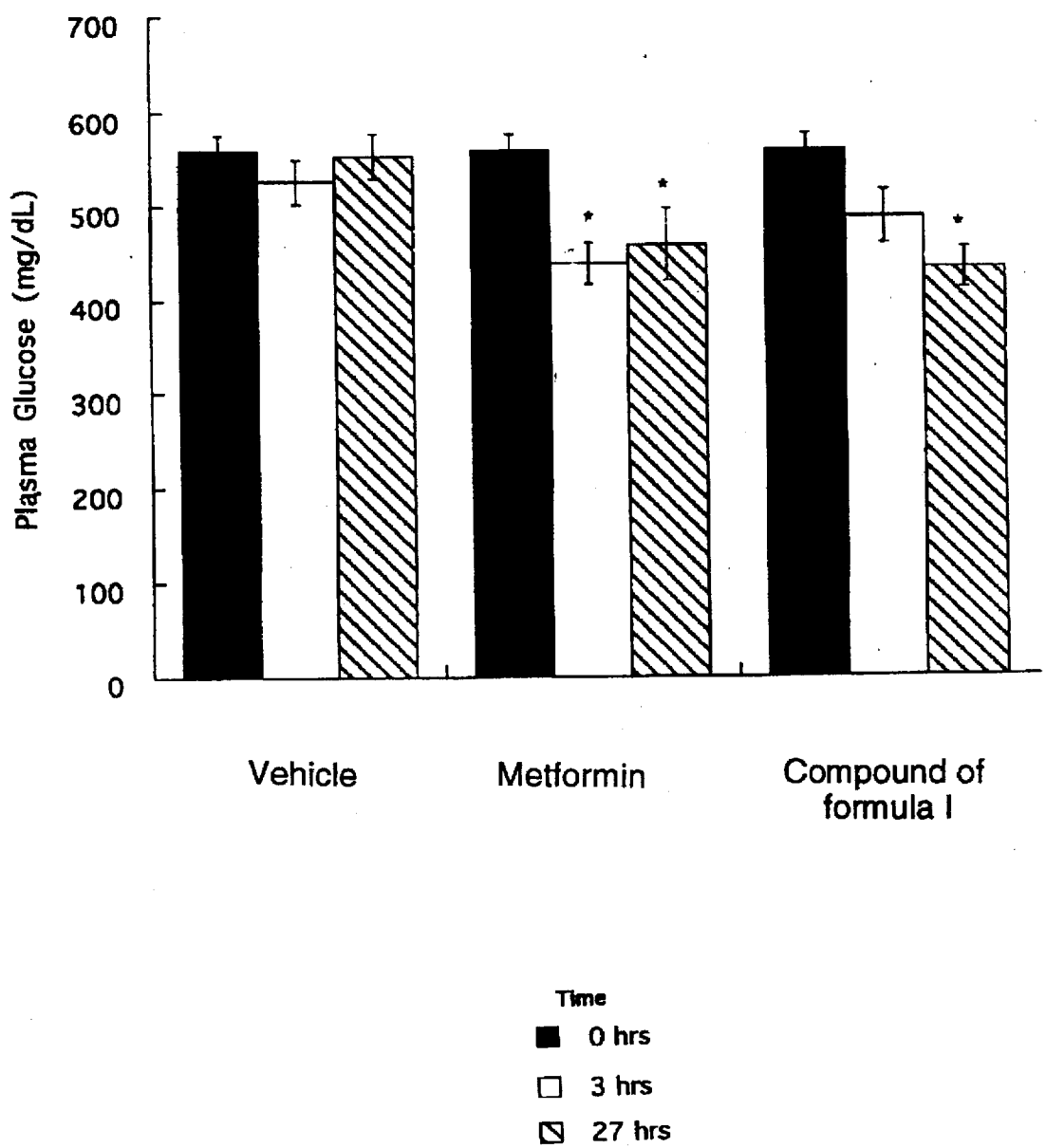

US005691386A

United States Patent [19]

Inman et al.

[11] Patent Number: 5,691,386
[45] Date of Patent: Nov. 25, 1997

[54] TRITERPENOID COMPOUND FOR THE TREATMENT OF DIABETES

[75] Inventors: Wayne D. Inman, Belmont; Michael John Reed, Menlo Park, both of Calif.

[73] Assignee: Shaman Pharmaceuticals, Inc., South San Francisco, Calif.

[21] Appl. No.: 633,396

[22] Filed: Apr. 16, 1996

[51] Int. Cl.⁶ .................................................. A61K 31/12
[52] U.S. Cl. ........................................ 514/691; 568/368
[58] Field of Search .............................. 514/691; 568/368

[56] References Cited

PUBLICATIONS

Bouboutou et al, Chem. Abst.; vol. 119, #271,442u (1993).
Pradham et al, Indian J. of Chem., vol. 32B, pp. 920–923 (1993).
Burkhill et al., *A Dictionary of the Economic Products of the Malay Peninsula*, (Ministry of Agriculture and Co-operative, Kuala, Lumpur, Malaysia) vol. II, pp. 1976–1977 (1966).
Heymann et al., "Characterization of Two Substances Isolated from an Indian Shrub", JACS 76(4):3689–3693 (1954).
John, "One Hundred Useful Raw Drugs of the Kani Tribes of Trivandrum Forest Division, Kerala, India", Int. J. Crude Drug Res. 22(1):17–39 (1984).
Joshi et al., "Triterpenes of *Salacia prinoides* DC", Tetrahedron 29:1365–1374 (1973).
Karunanayake et al., "Mangiferin from the Root Bark of *Salacia reticulata*", J. Ethnophamacology 13:227–228 (1985).
Krishnan et al., "Proanthocyaniding of *Salacia chinensis* Linn.", Tetrahedron Letters 26:2441–2446 (1967).
Mehra et al., "Pharmocognosy of Saptrangi—Antidiabetic Drug of Indian Origin", Research bulletin (N.S.) of the Panjab University 20(III–IV):487–502 (1969).
Quisumbing, *Medicinal Plants of the Phillippines*, (Republic of the Phillipines Department of Agriculture and Natural Resources), Technical Bulletin, 16, p.546 (1951).
Serasinghe et al., "Oral Hypoglycemic Effect of *Salacia reticula* in the Streptozoticin Induced Diabetic Rat", Pytotherapy Research, 4(5):205–206 (1990).
Venkateswarlu et al., "Pharmaceutical Investigations of a Film Forming Material Isolated From Roots of *Salacia macrosperma*", Drug Development and Industrial Pharmacy 19(4):461–472 (1993).

*Primary Examiner*—James H. Reamer
*Attorney, Agent, or Firm*—Pennie & Edmonds

[57] ABSTRACT

A novel hypoglycemically active triterpenoid compound isolated in purified, preferably substantially purified, form from Salacia spp., processes for obtaining the novel triterpenoid compound, compositions comprising the triterpenoid compound and methods for use a hypoglycemic agent, for example, in the treatment of diabetes, are described. In a preferred embodiment, the triterpenoid compound is obtained from *Salacia prinoides*. As an agent for the treatment of diabetes, the novel triterpenoid is useful for treating insulin-dependent (type I) and/or non-insulin-dependent (type II) diabetes.

13 Claims, 1 Drawing Sheet

TRITERPENOID COMPOUND FOR THE TREATMENT OF DIABETES

TABLE OF CONTENTS
1. FIELD OF THE INVENTION
2. BACKGROUND OF THE INVENTION
3. SUMMARY OF THE INVENTION
4. DESCRIPTION OF THE FIGURES
5. DETAILED DESCRIPTION OF THE INVENTION
   5.1 TRITERPENOID HYPOGLYCEMIC AGENT
   5.2 PROCESSES FOR ISOLATING THE TRITERPENOID COMPOUND OF FORMULA I
      5.2.1 ISOLATION AND PURIFICATION OF THE TRITERPENOID COMPOUND OF FORMULA I
   5.3 METHODS FOR USE OF THE TRITERPENOID COMPOUND OF FORMULA I
6. EXAMPLE: ISOLATION AND CHARACTERIZATION OF THE COMPOUND OF FORMULA I
   6.1 MATERIALS AND METHODS
   6.2 ISOLATION OF THE COMPOUND OF FORMULA I
   6.3 STRUCTURE ELUCIDATION OF THE TRITERPENOID COMPOUND OF FORMULA I
7. EXAMPLE: REDUCTION OF PLASMA GLUCOSE
   7.1 MATERIALS AND METHODS
   7.2 RESULTS

1. FIELD OF THE INVENTION

The present invention relates to a novel triterpenoid compound, 3β,30-dihydroxylup-20(29)-en-2-one, which exhibits hypoglycemic and/or antidiabetic activity in mammals, and provides processes for its isolation in purified, preferably substantially purified form, compositions comprising the triterpenoid compound in substantially purified form, and methods for use of the triterpenoid compound and compositions comprising the triterpenoid compound.

2. BACKGROUND OF THE INVENTION

Plants of the genus Salacia, e.g., *S. chinensis* L. (syn. *S. prinoides* DC.), and *S. reticulata* Wight (family Celastraceae, order Celastrales) have been used in India and in countries in Southeast Asia, including Sri Lanka, Burma, China, the Philippines, Malaysia, N. Queensland, Papua New Guinea, the Solomon Islands and Fiji, to treat a variety of ailments. For example, *Salacia prinoides* has been used in India as a tonic and blood purifier (H. Heymann et al., *J Amer Chem Soc* 76:3689–3693 (1954)) and also to treat jaundice (D. John, *Int J Crude Drug Res* 22(1):17–39 (1984)). In the Philippines, a hot water extraction of *Salacia prinoides* has been taken orally to treat amenorrhea and dysmenorrhea, and has also been used as an abortifacient (E. Quisumbing, *Tech Bull* 16, Rep philippines, Dept Agr Nat Resources, Manilla 1951:1 (1951) & *Dictionary of the Economic Products of the Malay Peninsula.*, Ministry of Agriculture and Cooperatives, Kuala Lumpur, Malaysia, Volume ii, Burkill, in book 1 (1966)).

Plants of the genus Salacia have also been used to treat diabetes. In India, a hot water extraction of the whole plant *Salacia prinoides* has been taken orally as an anti-diabetic (P. N. Mehra et al., *Res Bull Panjab Univ Sci* 20:487–502 (1969)) and dried parts of the plant including the rootbark (V. Krishnan et al., *Tetrahedron Lett.*, 26:2441–2446 (1967); P. N. Mehra et al., *Res Bull Panjab Univ Sci* 20:487–502 (1969); B. S. Joshi et al., *Tetrahedron* 29:1365–1374 (1973); V. Venkateswarlu et al. *Drug Dev Ind Pharm* 19(4):461–472 (1993)) have been used to treat diabetes. In Sri Lanka, aqueous extracts of the roots of *Salacia reticulata* have been used in the treatment of diabetes mellitus (E. H. Karunanayake et al., *J Ethnopharmacol* 13(2):227–228 (1985); S. Serasinghe et al., *Phytother Res* 4(5):205–206 (1990)).

While extracts of the genus Salacia have been used medicinally, such use is not without potential drawbacks. First, in addition to containing one or more compounds having a "desired" biological activity, plant species often contain a myriad of naturally-occurring organic compounds among which one or more can elicit a physiological or pharmacological response that is in contradiction with the desired activity. Secondly, plant species, even those considered to have medicinal properties, can contain countless toxic compounds. Thirdly, when administered in the form of a plant extract, the actual dosage of the active compound(s) is rarely possible to regulate, which can result in an ineffective amount, i.e, too low a concentration, or a toxic amount, i.e., too high a concentration, of active compound administered.

Thus, there is a need for a purified form, preferably a substantially purified form of an active compound obtainable from the genus Salacia useful as a hypoglycemic agent, compositions comprising therapeutically effective amounts of such a compound and methods for their use.

Citation or identification of any reference in Section 2 of this application shall not be construed as an admission that such reference is available as prior art to the present invention.

3. SUMMARY OF THE INVENTION

The present invention provides a novel triterpenoid compound, 3β,30-dihydroxylup-20(29)-en-2-one, as well as pharmaceutically acceptable salts thereof, having hypoglycemic activity, hypoglycemic compositions comprising the novel triterpenoid compound in purified, preferably substantially purified, form, as well as methods for their use.

Particularly, the present invention provides a novel triterpenoid compound, 3β,30-dihydroxylup-20(29)-en-2-one, having the structure of formula I:

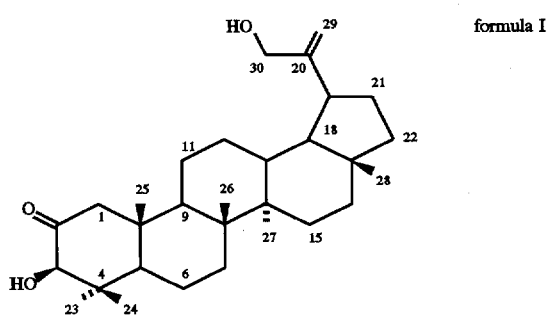

formula I and pharmaceutically acceptable salts thereof, for use as a hypoglycemic agent.

The invention further encompasses compositions comprising the triterpenoid compound in purified form, preferably in substantially purified form, or pharmaceutically acceptable salts thereof for use as hypoglycemic agents, e.g., to reduce blood glucose or treat diabetes mellitus, in mammals. Such compositions optionally contain a pharmaceutically acceptable carrier or vehicle and optionally other hypoglycemic agent(s) useful for the treatment of diabetes.

Still further, the invention encompasses methods for using the triterpenoid compound or compositions comprising the triterpenoid compound, as hypoglycemic agents.

The present invention may be understood more fully by reference to the following figures, detailed description and illustrative examples which are intended to exemplify non-limiting embodiments of the invention.

4. DESCRIPTION OF THE FIGURE

FIG. 1 is a bar graph showing the plasma glucose levels (mg/dL) of diabetic (db/db) mice treated with vehicle only, 250 mg/kg of metformin and 250 mg/kg of the present triterpenoid compound. The animals were dosed at 0 and 24 h, and plasma glucose levels were measured at 0, 3 and 27 h. All data points N=8. *P<0.05 (analysis of variance (ANOVA), one factor).

5. DETAILED DESCRIPTION OF THE INVENTION

5.1 TRITERPENOID HYPOGLYCEMIC AGENT

The novel triterpenoid compound of the present invention useful as a hypoglycemic agent is represented by the structure of formula I:

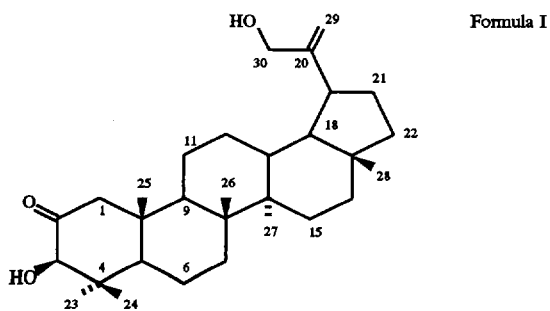

Formula I and pharmaceutically acceptable salts thereof. Such pharmaceutically acceptable salts are known to those skilled in the art and include, but are not limited to, sodium, potassium, lithium, calcium, magnesium, zinc and iron salts. As used herein, "triterpenoid" refers to the triterpenoid of the present invention, having the structure of formula I.

The compound of formula I can be obtained in purified form, preferably in substantially purified form, via extraction from Salacia spp. followed by column chromatography (see Section 5.2, below) or from conventional organic synthesis.

5.2 PROCESSES FOR ISOLATING THE TRITERPENOID COMPOUND OF FORMULA I

The compound of formula I can be isolated in purified form or substantially purified form from Salacia spp., preferably Salacia prinoides, using the illustrative methods described below or other standard extraction and purification techniques known to those of ordinary skill in the art.

5.2.1 ISOLATION AND PURIFICATION OF THE TRITERPENOID COMPOUND OF FORMULA I

Plant material from Salacia spp., preferably Salacia prinoides, is first extracted into an organic solvent, including non-polar organic solvents, polar organic solvents, or mixtures thereof, to obtain an organic solution of the present triterpenoid compound. By "plant material" is meant any part of the plant such as the leaves and roots, preferably the stems. Useful non-polar organic solvents include, but are not limited to, carbon tetrachloride, dichloromethane, benzene, toluene, xylenes, pentane, hexane, heptane and the like. Useful polar organic solvents include, but are not limited to, methanol, ethanol, isopropanol, acetone, 2-butanone, ethyl acetate, diethyl ether, tetrahydrofuran, chloroform, dimethylformamide, N-methylpyrrolidinone, dimethyl sulfoxide, and mixtures thereof. Preferably the solvent used to extract the compound of formula I from Salacia spp. is a non-polar organic solvent, most preferably hexane. Prior to extraction with the non-polar or polar organic solvent, the plant material may be optionally ground, shredded, macerated, or otherwise treated to increase its overall surface area.

Extraction of Salacia spp. with the non-polar or polar organic solvent can be accomplished using a Soxhlet-type extraction apparatus wherein small pieces of Salacia spp. are placed inside a porous thimble and continuously extracted with the non-polar or polar organic solvent at reflux temperatures for several hours to several days, or preferably, by simply placing small pieces of Salacia spp. into a vessel containing non-polar or polar solvent and allowing the resulting mixture to steep or stir at room temperature for several hours to several weeks.

Following extraction, the organic solution is concentrated (i.e., evaporated), optionally in vacuo, to obtain a non-polar or polar extract comprising the compound of formula I.

The non-polar or polar extract is then purified to afford the compound of formula I in purified form. By "purified form" is meant a non-naturally occurring, isolated form of the compound of formula I having a level of purity of at least 50%, preferably at least 90%, and most preferably at least 95%. The non-polar or polar extract can be purified via recrystallization or preferably, column chromatography, including conventional silica gel chromatography, vacuum-flash chromatography and preparative or semi-preparative high-performance liquid chromatography. When column chromatography is used to purify the compound of formula I from the non-polar or polar extract, it may be necessary to use several iterations of column chromatography to obtain the compound of formula I having the desired level of purity. Preferably, the non-polar or polar extract is first purified using conventional silica gel chromatography to afford a series of fractions that are enriched with the compound of formula I. These fractions are preferably repurified, more than once if required, to afford the compound of formula I in substantially purified form. By "substantially purified form" is meant a non-naturally occurring, isolated form of the compound of formula I having a level of purity of at least 95%. Purified and substantially purified forms of the triterpenoid compound of formula I can be obtained by purification of materials isolated by extraction from natural plant sources, such as Salacia spp., preferably Salacia prinoides, or by purification of compounds obtained from a chemical synthesis process.

5.3 METHODS FOR USE OF THE TRITERPENOID COMPOUND OF FORMULA I

Due to the potent hypoglycemic activity of the triterpenoid compound of the present invention, the triterpenoid compound of formula I is advantageously useful in veterinary and human medicine for therapeutic treatment of diabetes mellitus. Additionally, the triterpenoid compound can be advantageously used as a hypoglycemic agent to reduce the blood glucose level in situations of acute stress such as experienced by animals or patients with hyperthermia, trauma, sepsis, and burns and undergoing general anesthesia. Hyperglycemia sometimes associated with severe head injury, cerebral thrombosis, encephalitis and heat stroke can also be therapeutically treated with the compound of formula I. Additionally, the triterpenoid compound is useful as a hypoglycemic agent for rare congenital metabolic glycogen storage disease associated with hyperglycemia.

Although the present inventor does not wish to be limited to any particular mechanism of action to explain the hypoglycemic activity of the triterpenoid compound of the present invention, it is envisaged that it may advantageously be useful for treatment of both insulin-dependent or type I diabetes (formerly termed juvenile-onset or ketosis-prone diabetes) and non-insulin-dependent or type II diabetes (formerly termed adult-onset, maturity-onset or nonketotic diabetes).

When administered to a mammal for veterinary use or to a human for clinical use, the compound of formula I is administered in purified, preferably substantially purified form. The triterpenoid compound of formula I can be administered alone, or in the form of a composition comprising any physiologically acceptable carrier such as water, an aqueous solution, normal saline, or other physiologically acceptable excipient. In general, the therapeutically effective dosage would range from about 10–1000 mg/kg/day, preferably about 1–250 mg/kg/day. It is to be understood that when combined with a vehicle or excipient for administration to mammal, the compound of formula I is used in purified, preferably substantially purified form in conjunction with the vehicle or excipient.

The triterpenoid compound of formula I or composition comprising the triterpenoid compound of formula I can be administered by a number of routes, including, but not limited to: orally, injection including, but not limited to intravenously, intraperitoneally, subcutaneously, intramuscularly, etc. The preferred route of administration is oral. The compositions can additionally contain other hypoglycemic agents such as insulin; a biguanide such as metformin or buformin; a sulfonylurea such as acetohexamide, chlorpropamide, tolazamide, tolbutamide, glyburide, glypizide or glyclazide; a thiazolidinedione such as troglitazone; an a-glycosidase inhibitor such as acarbose or miglatol; or a P3-adrenergic receptor agonist such as CL-316, 243, etc; or mixtures thereof.

The triterpenoid compound of the present invention can optionally be administered in an effective amount as a pharmaceutically acceptable salt using counter ions such as sodium, potassium, lithium, calcium, magnesium, zinc and iron.

In addition, the triterpenoid compound or pharmaceutically acceptable salts thereof can be used for research purposes, for example, to investigate the mechanism and activity of hypoglycemic agents.

The following series of Examples are presented by way of illustration and not by way of limitation on the scope of the invention.

6. EXAMPLE: ISOLATION AND CHARACTERIZATION OF THE COMPOUND OF FORMULA I

6.1 MATERIALS AND METHODS

Analytical high performance liquid chromatography (HPLC) was performed on a Hitachi Model D-6500 Chromatography Data Station equipped with a L-6200A pump, AS2000 autosampler, L-4500 A diode array detector and a Sedex 55 light scattering detector connected in parallel. Columns used in analytical HPLC were an ODS-AQ (YMC Inc.), 4×50 mm (3 µm). Semi-preparative HPLC was performed on a Hitachi Model D-6500 Chromatography Data Station equipped with a Waters 600 pump controller, an L-4500 A diode array detector, and an L-5200 Hitachi fraction collector. Columns used in semipreparative HPLC were an ODS-AQ (YMC Inc.), 20×150 mm (5 µm) equipped with a 20×50 mm guard column, and a silica (YMC Inc.), 20×250 mm (5 µm) column and 20×50 mm guard column. Preparative HPLC chromatography was performed with a Rainin Dynamax HPLC system equipped with a Dynamax Diode Array Detector (Model PDA-1) and solvent delivery pumps (Model SD-1), and interfaced with a Dynamax PC HPLC Data System. A silica (Kromasil NP, 10 µm, 120 Å pore size) 50×250 mm column and 50×30 mm guard column and Primesphere C18 HC (10 gm) 50×250 mm with a 50×30 mm guard column were used in the preparative HPLC. All chromatographic runs were performed at ambient temperature. HPLC grade or ACS grade solvents were used without further purification.

Nuclear magnetic resonance (NMR) spectra were recorded on a Varian Unity Plus 400 or a Varian Unity 400 spectrometer. NMR spectra of compounds were recorded in deuterated chloroform. One and two-dimensional NMR experiments, including Distortionless Enhancement Polarization Transfer (DEPT), H-H Correlation Spectroscopy (COSY), Heteronuclear Multiple Quantum Correlation (HMQC), Heteronuclear Multiple Bond Correlation (HMBC), long-range Heteronuclear Chemical Shift Correlation (HETCOR) provided molecular structure information. MS spectra were recorded on a Kratos MS-50 in high resolution power electron impact scanning mode, 70 ev. Resolution was set to 2000, scanning rate 10 sec/decay, temperature gradient from 50° to 300° C. increased at a rate of 50°/min. IR spectra were recorded on a Perkin-Elmer 1600 Series FTIR. UV spectra were recorded on a Perkin-Elmer Lambda 2 UV/VIS spectrometer or taken directly from the Hitachi diode-array UV detector on the HPLC system. Melting points were measured on a Buchi 535 melting point apparatus and are uncorrected.

6.2 ISOLATION OF THE COMPOUND OF FORMULA I

Isolation of the compound of formula I is summarized below in Scheme 1. Shredded and ground whole plant material from *Salacia prinoides* (5 kg) was added to a 75 L vessel and allowed to stir in 50 L of hexane for six hours at room temperature, and then steep overnight. Evaporation of the hexane yielded 29.2 g of a hexane extract. The hexane extract was fractionated by vacuum flash chromatography using the following protocol. The hexane extract was dissolved in a minimum amount of dichloromethane and added to 150 mL of silica gel (230–400 mesh, 60 Å). The resulting silica gel slurry was then dried using rotary evaporation and then added to the top of 250 mL of clean silica gel in a 600 mL (10 cm i.d.) vacuum funnel producing a final bed size of 10×6 cm. The column of silica gel within the vacuum funnel was eluted under vacuum, with 1:5 ethyl acetate:hexane, providing fraction 1 (F1); 1:1 ethyl acetate:hexane, providing fraction 2 (F2); and then with methanol, providing fraction 3 (F3). F2 was concentrated to provide 5.63 g of a crude fraction comprising the compound of formula I. 4.54 g of this crude fraction comprising the compound of formula I was further purified by HPLC on a silica 10 µm (Kromasil) 50×250 mm column equipped with a precolumn (50×30 mm) eluting with a linear gradient of hexane and isopropyl alcohol at a flow rate of 60 mL/min. In this manner, 0.716 g of a purified fraction comprising the compound of formula I was obtained, being >50% pure. The compound of formula I was obtained in substantially purified form using semi-preparative HPLC on a silica 5 μm (YMC Inc.) 20×250 mm column equipped with a 20×30 mm guard column to yield 338 mg of triterpenoid compound of formula I.

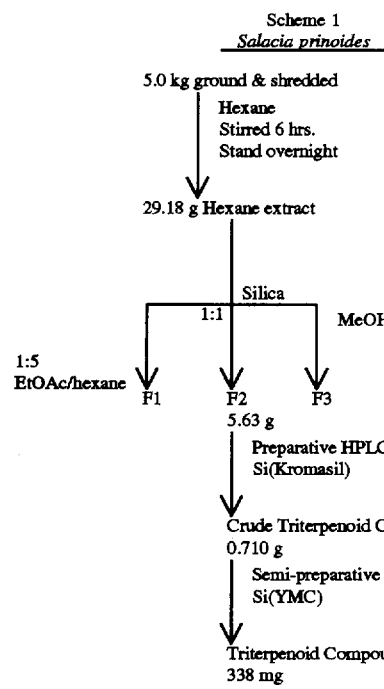

Scheme 1
*Salacia prinoides*

6.3 STRUCTURE ELUCIDATION OF THE TRITERPENOID COMPOUND OF FORMULA I

The triterpenoid compound of formula I was obtained from semi-preparative HPLC, described above in Section 6.2, as an amorphous solid, m.p. 94.5° to 95.1°, $[\alpha]_D$+7.6° (c 1.32), and identified as 3β,30-dihydroxylup-20(29)-en-2-one. Its IR spectrum indicated the presence of hydroxyl groups at 3478 cm$^{-1}$ and a keto functionality at 1712 cm$^{-1}$. Its molecular formula, $C_{30}H_{48}O_3$, was determined by HRE-IMS m/z 456.3592 (M+, 1.1 mmu of calc.) and by a DEPT $^{13}$C NMR spectrum. Table 1 lists the assigned $^{13}$C and $^1$H chemical shifts for the compound of formula I. Assignments are based on one and two-dimensional NMR experiments known to those skilled in the art of organic compound structure elucidation and include Distortionless Enhancement Polarization Transfer (DEPT), H-H Correlation Spectroscopy (COSY), Heteronuclear Multiple Quantum Correlation (HMQC), Heteronuclear Multiple Bond Correlation (HMBC) and long-range Heteronuclear Chemical Shift Correlation (HETCOR) experiments. In addition, chemical shift assignments for the triterpenoid compound of formula I were based on values reported for related lupenone compounds (W. F. Tinto, L. C. Blair, A. Alli, W. F. Reynolds, S. McLean, *J. Nat. Prod.*, 55, 395, 1992). The stereochemistry of the hydroxyl group at C-3 was assigned having a β configuration and was based on the $^{13}$C chemical shifts of C-5, C-23 and C-24, which are strongly influenced by the stereochemistry of the hydroxyl group at C-3 (S. S. Kang, *Korean J. Pharmacogn.*, 18, 151, 1987). The reported $^{13}$C chemical shift values for C-5, C-23 and C-24 in 3β,28-dihydroxy-20(29)-lupene (betulin, S. Siddigui, F. Hafeez, S. Begum, B. S. Siddigui, *J. Nat. Prod.*, 51, 229, 1988), 3α, 11α-dihydroxy-20(29)-lupen-28-oic acid (S. K. Srivastava, *J. Nat. Prod.*, 55, 298, 1992), and the triterpenoid compound of formula I are shown below in Table 2. A good correlation between the C-5, C-23 and C-24 chemical shifts of the known compound betulin and the triterpenoid compound of the present invention suggests that the C-3 hydroxyl group of the compound of formula I is in the β configuration.

TABLE 1

Carbon and Proton Chemical Shifts and Multiplicities for the Triterpenoid Compound of Formula I (Chemical shifts are measured in CDCl$_3$ at 100 MHz for $^{13}$C and 400 MHz for $^1$H.)

| Atom # | C13 | | H | |
|---|---|---|---|---|
| 1 | 53.4 | (t) | 1.94 | (1H, d, 12 Hz) |
| | | | 2.45 | (1H, d, 12 Hz) |
| 2 | 211.4 | (s) | | |
| 3 | 82.8 | (d) | 3.81 | (1H, d, 4.8 Hz) |
| 4 | 45.5 | (s) | | |
| 5 | 54.5 | (d) | 1.34 | (1H, m) |
| 6 | 18.4 | (t) | 1.38 | (1H, m) |
| | | | 1.59 | (1H, m) |
| 7 | 33.7 | (t) | 1.41 | (2H, m) |
| 8 | 41.2 | (s) | | |
| 9 | 50.2 | (d) | 1.52 | (1H, dd, 12, 4 Hz) |
| 10 | 43.8 | (s) | | |
| 11 | 21.1 | (t) | 1.22 | (2H, m) |
| 12 | 26.3 | (t) | 1.05 | (1H, m) |
| | | | 1.37 | (1H, m) |
| 13 | 37.8 | (d) | 1.60 | (1H, m) |
| 14 | 42.8 | (s) | | |
| 15 | 27.3 | (t) | 0.98 | (1H, m) |
| | | | 1.63 | (1H, m) |
| 16 | 35.3 | (t) | 1.33 | (1H, m) |
| | | | 1.46 | (1H, m) |
| 17 | 42.9 | (s) | | |
| 18 | 48.7 | (d) | 1.42 | (1H, m) |
| 19 | 43.6 | (d) | 2.22 | (1H, ddd, 11, 11, 5 Hz) |
| 20 | 154.5 | (s) | | |
| 21 | 31.6 | (t) | 2.02 | (1H, dddd, 11, 11, 2, 2 Hz) |
| | | | 1.3 | (1H, m) |
| 22 | 39.7 | (t) | 1.35 | (1H, m) |
| | | | 1.18 | (1H, m) |
| 23 | 29.2 | (q) | 1.11 | (3H, s) |
| 24 | 16.3 | (q) | 0.62 | (3H, s) |
| 25 | 16.9 | (q) | 0.73 | (3H, s) |
| 26 | 15.6 | (q) | 0.97 | (3H, s) |
| 27 | 14.5 | (q) | 0.93 | (3H, s) |
| 28 | 17.6 | (q) | 0.72 | (3H, s) |
| 29 | 106.8 | (t) | 4.88 | (1H, dddd, 1, 1, 1, 1 Hz) |
| | | | 4.84 | (1H, s) |
| 30 | 64.8 | (t) | 4.07 | (1H, d, $J_{AB}$ = 14 Hz) |
| | | | 4.03 | (1H, d, $J_{AB}$ = 14 Hz) |
| $C_3$—OH | — | | 3.44 | (1H, d, 4.8 Hz) |
| $C_{30}$—OH | — | | 3.41 | (1H, s) |

TABLE 2

Carbon Chemical Shifts (ppm)

| | Betulin | 3α,11α-dihydroxy-20(29)-lupen-28-oic acid | Compound of Formula I |
|---|---|---|---|
| C-5 | 55.4 | 49.4 | 54.5 |
| C-23 | 28.0 | 29.6 | 29.2 |
| C-24 | 15.3 | 22.7 | 16.3 |

7. EXAMPLE: REDUCTION OF PLASMA GLUCOSE

This example illustrates the effectiveness of the triterpenoid compound of formula I in reducing plasma glucose levels in obese diabetic db/db mice, i.e., an art-recognized model of non-insulin dependent diabetes mellitus (NIDDM) useful in predicting hypoglycemic activity in mammals, including humans.

7.1 MATERIALS AND METHODS

Genetically altered obese diabetic mice (designated C57BUKs-db/db) were purchased from the Jackson Laboratory (Bar Harbor, Me., USA), and served as experimental animals. Male animals between the ages of 8–9 weeks were employed in the studies described here. Animals were housed (4 mice/cage) under standard laboratory conditions at 22° C. and fed Purina rodent chow and water ad libitum. Prior to treatment, blood was collected from the tail vein of each animal. Mice that had plasma glucose levels between 350 and 600 mg/dl were used in this experiment. Each treatment group consisted of eight mice that were distributed so that mean glucose levels were equivalent in each group at the start of the study. Diabetic mice designated C57BLIKS-db/db were dosed orally by gavage once daily for 2 days with either vehicle, the compound of formula I administered at 250 mg/kg/q.d., or metformin [250 mg (1510 µmol)/kg/day]. Compounds were delivered in vehicle formulation appropriate for each compound; e.g., including components such as 0.25% (w/v) carboxymethylcellulose, and up to 10% (v/v) dimethyl sulfoxide (DMSO) in a volume of 10 ml/kg. Blood was sampled from the tail vein three hours post-dosing in non-fasted conditions (3 h and 27 h samples). Blood samples were analyzed for plasma glucose levels. Individual body weights and mean food consumption (each cage) were also measured after 27 h.

The triterpenoid compound of formula I was prepared in substantially purified form as described above in Section 6.2 above. Metformin (1,1-dimethylbiguanide) was purchased from Sigma Chemical Co. (St. Louis, Mo., USA; catalog # D5035).

Plasma glucose levels were determined colorimetrically using a glucose oxidase assay (Sigma Chemical Co.; Sigma catalog #325). Significant differences between groups (comparing compound-treated to vehicle-treated) were evaluated using analysis of variance and Fisher's post-hoc test.

7.2 RESULTS

As shown in FIG. 1 and below in Table 3, oral administration of the triterpenoid compound of formula I to diabetic C57BL/Ks-db/db mice once daily for 2 days at a dosage level of 250 mg/kg/dose resulted in a −127.6 (mg/dL) change in plasma glucose, i.e., a statistically significant reduction, relative to vehicle (control) after 27 h. By comparison, the known hypoglycemic agent metformin, administered at 250 mg/kg, caused a reduction in plasma glucose levels of only 100.8 mg/dL at the same interval. In addition, as shown below in Table 4, the change in body weight and overall food consumption values for mice administered with the compound of formula I were comparable to those values obtained for mice administered with metformin.

These data indicate that the triterpenoid compound of formula I is an effective hypoglycemic agent in a rodent model of insulin resistance, obesity and NIDDM.

TABLE 3

Effects of Test Compounds on Blood Glucose in Diabetic db/db Mice

| Treatment | Dose (mg/kg) | Change in Glucose (mg/dL) 3 h | P Value* | Change in Glucose (mg/dL) 27 h | P Value* |
|---|---|---|---|---|---|
| Vehicle | — | −33.0 | NS | −6.2 | NS |
| Metformin | 250 | −120.7 | 0.0121 | −100.8 | 0.0312 |
| Compound of Formula I | 250 | −72.6 | NS | −127.6 | 0.0066 |

NS = not significant

TABLE 4

Effects of Test Compounds on Body Weight and Food Consumption in Diabetic db/db Mice

| Treatment | Dose (mg/kg) | Change in Body Weight (g) 24 h | Food Consumption (g/mouse) 0–24 h |
|---|---|---|---|
| Vehicle | — | 0.0 | 7.1 |
| Metformin | 250 | −0.4 | 5.4 |
| Compound of Formula I | 250 | −0.2 | 5.3 |

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited and the entire disclosures of which are incorporated herein by reference.

What is claimed is:

1. A purified compound having the structure of formula I:

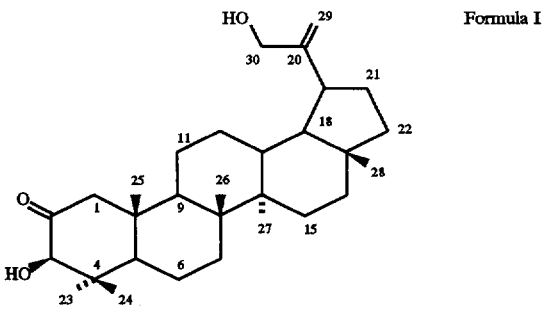

Formula I and pharmaceutically acceptable salts thereof.

2. The compound of claim 1, wherein the pharmaceutically acceptable salt is selected from the group consisting of sodium, potassium, lithium, calcium, magnesium, zinc and iron.

3. A pharmaceutical composition for use as a hypoglycemic agent in mammals, comprising a therapeutically effective amount of the compound of claim 1 in substantially purified form.

4. The composition of claim 3 further comprising a hypoglycemic agent selected from the group consisting of a sulfonylurea, a biguanide, a thiazolidinedione, a P3-adrenergic receptor agonist, an α-glycosidase inhibitor, insulin and mixtures thereof.

5. The composition of claim 4 wherein the sulfonylurea is selected from the group consisting of acetohexamide, chlorpropamide, tolazamide, tolbutamide, glyburide, glypizide and glycazide.

6. The composition of claim 4, wherein the biguanide is metformin or buformin.

7. The composition of claim 4, wherein the α-glucosidase inhibitor is acarbose or miglatol.

8. The composition of claim 4, wherein the thiazolidinedione is troglitazone.

9. A method for reducing the blood glucose of a mammal, comprising administering to said mammal in need of such blood glucose reduction, a hypoglycemically effective amount of the composition of claim 1.

10. A method for reducing the blood glucose of a mammal, comprising administering to said mammal in need of such blood glucose reduction, a hypoglycemically effective amount of the composition of claim 3.

11. A method for treatment of diabetes mellitus, comprising administering, to a mammal suffering from diabetes mellitus, a therapeutically effective amount of the composition of claim 3.

12. A method for reducing the blood glucose of a mammal, comprising administering to said mammal in need of such blood glucose reduction, a hypoglycemically effective amount of the composition of claim 4.

13. A method for treatment of diabetes mellitus, comprising administering, to a mammal suffering from diabetes mellitus, a therapeutically effective amount of the composition of claim 4.

* * * * *